United States Patent [19]

Kusakawa et al.

[11] Patent Number: 5,204,375
[45] Date of Patent: Apr. 20, 1993

[54] BETAINE SURFACE ACTIVE AGENT HAVING AN ESTOLIDE HYDROPHOBIC GROUP

[75] Inventors: Susumu Kusakawa, Hazuyama; Yoshiyuki Itoh, Hinaganishi; Yuka Saigusa, Tamanoi, all of Japan

[73] Assignee: Itoh Seiyu Kabushiki Kaisha, Mie, Japan

[21] Appl. No.: 820,036

[22] Filed: Jan. 14, 1992

[30] Foreign Application Priority Data

Jan. 16, 1991 [JP] Japan ................. 17102/1991

[51] Int. Cl.$^5$ ................. A61K 9/107; C07C 215/40; C07C 229/26; C07C 233/47
[52] U.S. Cl. ................. 514/784; 252/312; 252/356; 252/357; 252/527; 252/546; 252/DIG. 5; 252/DIG. 7; 426/519; 514/788; 514/846; 514/938; 554/52; 554/61; 554/63; 562/561
[58] Field of Search ................. 554/52, 61, 63; 562/561; 252/527, 546, 356, 357, 312, DIG. 5, DIG. 7; 426/519; 514/784, 788, 846, 938

[56] References Cited

U.S. PATENT DOCUMENTS

| | | | |
|---|---|---|---|
| 3,225,074 | 12/1965 | Cowen | 554/52 |
| 3,360,550 | 12/1967 | Cowen | 554/52 |
| 3,533,955 | 10/1970 | Pader | 252/153 |
| 4,137,191 | 1/1979 | Lohr | 252/153 |
| 4,221,733 | 9/1980 | Melloh et al. | 554/52 |
| 4,428,850 | 1/1984 | Zoleski | 252/42.7 |
| 4,582,715 | 4/1986 | Volpenhein | 426/601 |
| 4,857,216 | 8/1989 | Worschech | 252/39 |

*Primary Examiner*—Dennis Albrecht
*Attorney, Agent, or Firm*—Armstrong, Westerman, Hattori, McLeland & Naughton

[57] ABSTRACT

Lipophilic amphoteric surface active compositions exhibiting remarkable W/O emulsifying property and good stabililty against oxidation, comprising betaines having the general formula $$R_1-CO-NH-R_2-\overset{\underset{\displaystyle CH_3}{|}}{\underset{\underset{\displaystyle CH_3}{|}}{N^+}}-(CH_2)_n-COO^-$$

wherein $R_1$—CO is an acyl radical of estolides, $R_2$ is an alkylene group having 1 to 3 carbon atoms and n is an integer from 1 to 3.

9 Claims, No Drawings

BETAINE SURFACE ACTIVE AGENT HAVING AN ESTOLIDE HYDROPHOBIC GROUP

BACKGROUND OF THE INVENTION

1. Field of the Invention

The present invention relates to lipophilic amphoteric betaine compositions, which exhibit superiority in surface activity and oxidation stability to lecithin. Preparation method of the betaine compositions is also provided.

2. Description of the Prior Art

Lecithin

Lecithin has two fatty acid units and two hydrophilic groups in the molecule. The lipophilic balance makes lecithin useful. As a result, lecithin is widely used for baking products, margarine, ice cream, noodles, chocolate, cosmetics, instant foods, pharmaceuticals, sealing and caulking compounds, inks, paints, drugs and so on.

Lecithin occurs universally in living organisms. Commercial lecithins are derived almost entirely from soybeans and yolk.

Although color of lecithin is nearly white when freshly made, it rapidly becomes yellow to brown in air. This ready oxidation also causes other troubles such as peroxide formation and limits lecithin's applicable uses.

Other factors such as heat, light, metalic catalysts and pH are also considered to react on lecithin to autooxidize.

Hydrogenation of lecithins has been employed in order to settle the above-mentioned problem and hydrogenated lecithins have already been offered in the market. Hydrogenation weeds out oxidation troubles on lecithin, however, it considerably reduces lecithin's excellent emulsifying property and compatibility with other ingredients.

Betaine

Concerning synthetic amphoteric surfactants, betaines of the formula

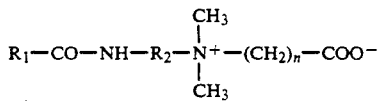

wherein $R_1$ is a long chain alkyl group, $R_2$ is a short chain alkylene group, and n is an integer from 1 to 3 are known.

These specific betaine compounds and their preparations are discussed in U.S. Pat. No. 2,866,423, West German Patent No. 1,062,392 and U.S. Pat. No. 4,137,191, where $R_1$ represents hydrocarbon radicals containing carbon atoms from 10 to 20 carbon atoms. Related compounds are also disclosed in U.S. Pat. No. 2,777,872 and in U.S. Pat. No. 2,961,451.

The same type of fatty acid amide betaine compositions are discussed in U.S. Pat. No. 4,221,733, where $R_1$—CO is an acyl radical of ricinoleic acid.

The ricinoleic acid amide betaine compositions are also useful in aqueous media such as cleansing, bathing and disinfecting compositions.

Since all of the above-mentioned synthetic betaine compositions have only one long alkyl or acyl group and two hydrophilic groups, namely quaternary ammonium group and carboxyl group in their molecule, these betaine compositions are not lipophilic but hydrophilic.

In U.S. Pat. No. 3,225,074 betaines having two long chain acyl groups are provided through the reaction between two moles of fatty acid and one mole of polyamines such as bis-(3-aminopropyl)-methylamine, dipropylenetriamine, diethylenetriamine and bis-(3-aminopropyl)-hydroxylethylamine.

In these cases, the betaines obtained have two long acyl groups and two amide groups in their molecules. Although the former (two acyl groups) imparts lipophilic property, the latter (two amide groups) greatly reduces lipophilic property and compatibility with non-polar substances. As a result, the betaines disclosed in U.S. Pat. No. 3,225,074 do not exhibit enough lipophilic property and do not form W/O emulsion with oily substances such as long chain fatty acid esters, hydrocarbons or silicones.

Estolide

Estolides can be prepared by the polycondensation of hydroxyfatty acids or mixtures of hydroxyfatty acids and ordinary non-hydroxy bearing fatty acids.

As a lipophilic surfactant, derivatives from estolides are known.

U.S. Pat. No. 2,785,978 discloses surface active compounds prepared by esterification between polycondensed hydroxycarboxylic acids having at least 8 carbons and polycondensed polyhydric alcohols having at least 3 carbon atoms. Their applications as an emulsifying agent for cosmetics and foods are also discussed in this patent.

U.S. Pat. No. 3,429,820 discloses power stering process and lubricating compositions containing estolides of 12-hydroxystearic acid having a neutlarization number of not more than 30.

SUMMARY OF THE INVENTION

It is an object of the present invention to provide betaines having improved lipophilic characteristics and good stability against oxidation.

Lipophilic amphoteric surface active compositions of the present invention comprises betaines having the general formula

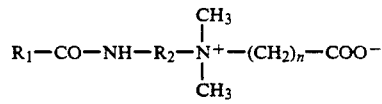

wherein $R_1$—CO is an acyl radical of estolides, $R_2$ is an alkylene group having 1 to 3 carbon atoms and n is an integer from 1 to 3.

Method of preparing lipophilic amphoteric surface active compositions of the present invention comprises the following 3-stage-reaction. The first stage reaction is an estolide-formation reaction by polycondensation of hydroxy-fatty acids or mixtures of hydroxyfatty fatty acids and ordinary non-hydroxy bearing fatty acids. The second stage reaction is an amide-tertiary amine intermediate-formation reaction of the estolides obtained in the first stage with diamines having one primary or secondary amino group and one tertiary amino group. The third stage reaction is a betaine-formation reaction by quaternarization of the amide-tertiary amine intermediates obtained in the second stage with omega-halogen-substituted aliphatic acids.

DETAILED DESCRIPTION OF THE INVENTION

In accordance with the present invention, betaines having improved lipophilic characteristics and good stability against oxidation are provided.

As stated above, the betaines of the present invention have the general formula

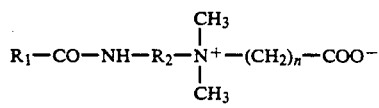

wherein $R_1$—CO is an acyl radical of estolides, $R_2$ is an alkylene group having 1 to 3 carbon atoms and n is an integer from 1 to 3.

The chain length of $R_1$—CO is very important and can be varied by controlling the degree of polycondensation in the process of estolide-formation reaction as described hereinafter.

The betaines of the present invention are obtained by the following 3-stage-reaction.

The first stage reaction

In the present invention, the term "polycondensation" is used as a reaction in which a number of molecules of fatty acids are inter-molecularly condensed to form estolides.

The first stage is the estolide-formation reaction by polycondensation of hydroxyfatty acids or mixtures of hydroxyfatty acids and ordinary non-hydroxy bearing fatty acids.

In the present invention, hydroxyfatty acids having at least 8 carbon atoms, preferably from 12 to 20 carbon atoms are used. Preferable hydroxyfatty acids are castor oil fatty acid (ricinoleic acid), hydrogenated castor oil fatty acid (12-hydroxystearic acid) and the mixtures containing them.

Other ordinary non-hydroxy bearing fatty acids may be used together with the hydroxyfatty acids unless they prevent enough estolide formation. Examples of the other ordinary non-hydroxy bearing fatty acids are lauric acid, myristic acid, palmitic acid, stearic acid, behenic acid, montanic acid, oleic acid, linolic acid, linolenic acid and so on.

The polycondensation reaction is carried out by heating these fatty acids. Suitable catalysts and some kind of solvents for azeotropic refluxing can preferably be used to the reaction mixture. An inert gas such as nitrogen or carbon dioxide may be passed through the reation mixture while heating is continued. The temperature of polycondensation reaction depends upon the nature of the fatty acids. Generally, the polycondensation reaction may be performed at a temperature from 170° to 230° C. for a period between about 2 to 15 hours, depending upon the degree of condensation desired.

Polycondensation of the fatty acid materials should be performed so as to provide an acid number preferably between 25 to 120 in the estolides obtained.

For example, castor oil fatty acid, which gives good results when used in the process of the present invention, may be heated in vacuum for about 6 hours at a temperature between about 170° and 200° C. The resulting polycondensed castor oil fatty acid has an acid number of 90. If the heating is continued for 10 hours, the acid number drops to 35.

Generally speaking, estolides having lower acid number not more than 60 are suitable for making an emulsifier for non-polar oily substance such as hydrocarbons (liquid paraffine, squalane, mineral oil, etc.) and silicones. Esteloides having an acid number of 60 to 120 are suitable for uses with esters.

The second stage reaction

The second stage reaction is the amide-tertiary amine intermediate-formation reaction of the estolides obtained in the first stage with diamines having one primary or secondary amino group and one tertiary amino group.

Representative examples of such diamines are N,N-dimethylaminopropylamine, N,N-diethylaminopropylamine, N,N-diethylaminoethylamine, N,N-dimethylaminoethylamine, N,N-diethylaminobutylamine, N,N-dimethylaminoethoxypropylamine, N-aminoethylmorpholin, N-aminopropylmorpholin, N-aminoethylpiperidine, N-aminopropylpiperidine, N-aminoethyl-4-pipecoline, N-aminopropyl-4-pipecoline, N-methylpiperazine, N-hydroxyethoxypiperazine, 2-methylaminoethylpyrdine and so on.

The third stage reaction

The third stage reaction is the betaine-formation reactionby quaternarization of the amide-tertiary amine intermediates obtained in the second stage with omega-halogen-substituted aliphatic acids.

The amide-tertiary amine intermediates are reacted with an omega-halogen-substituted aliphatic acid in the presence of an alkaline material such as an alkali metal or alkaline earth metal hydroxide or bicarbonate to form the desired betaines.

Representative examples of the omega-halogen-substituted aliphatic acids suitable for the present invention are α-chloroacetic acid, α-bromoacetic acid, β-chloropropionic acid, γ-chlorobutyric acid and so on.

The betaines obtained through the above-mentioned three stages have two or more long chain fatty acid units, one quarternary ammonium group and one carboxyl group in their molecule. Therefore, the betaines are lipophilic enough to be useful in oil phase or as a W/O emulsifier.

The Betaines of the present invention are also stable enough against oxidation, light and other natural circumstances to be used for cosmeticsand other uses.

The betaine compositions of the present invention may include minor amount (not more than 50 percent by weight) of other betaines such that $R_1$—CO is an acyl radical of uncondensed hydroxyfatty acid or ordinary non-hydroxy bearing fatty acid.

The present invention will be further illustrated by the following examples. It should be understood, however, that although these examples may describe in more particular detail some of the very specific features of the invention, they are given primarily for purposes of illustration and the invention in its broarder aspects is not to be construed as limited thereto.

EXAMPLES

Preparation of Betaine

EXAMPLE 1

641 grams (2.1 mole) of castor oil fatty acid having an acid number of 180, prepared by saponifying castor oil, was charged in a flask with a Dean-Sterk tube and a refluxcondenser, and was heated at a temperature between 170°–200° C. for 6 hours under nitrogen atmosphere during which time water was removed. At the end of this period, the acid number dropped to 90, which indicated that castor oil fatty acid changed into an estolide corresponding to the dimeric acid of castor oil fatty acid.

The estolide obtained was cooled to 80° C. and then was added 112 grams (1.1 mole) of N,N-dimethylaminopropylamine. The mixture was reacted at a temperature between 150°–190° C. under nitrogen atmosphere for 6 hours, which process was followed by removal of water and unreacted amine under vacuum at 120°–140° C.

705 grams of a yellow brown viscous liquid having an amine number of 85 was obtained.

Then, 99.0 grams of the amide intermediate was placed in a flask with a reflux condenser, and was added 127 grams of monochloroacetic acid solution (14 grams of monochloroacetic acid and 13 grams of sodium bicarbonate in 100 grams of isopropyl alcohol). The reaction mixture was maintained at 80° C. for 6 hours under stirring, and then was filtered with some celite. After removal of isopropyl alcohol, 106 grams of a yellow pasty betaine was obtained.

EXAMPLE 2

In the same manner as Example 1, 390 grams (1.27 mole) of castor oil fatty acid was heated to form an estolide having an acid number of 45, which indicated that the estolide corresponded to the tetramer of castor oil fatty acid.

To the estolide obtained 32 grams (0.32 mole) of N,N-dimethylaminopropylamine was added and the mixture was reacted in the same manner as Example 1. A yellow brown liquid having an amine number of 46 was obtained.

To 120 grams of the intermediate obtained was added 148 grams of monochloroacetic acid solution (9.5 grams of monochloroacetic acid and 8.5 grams of sodium bicarbonate in 130 grams of isopropyl alcohol). The reaction mixture was treated in the same manner as the previous example and 125 grams of a brown liquid was obtained.

EXAMPLE 3

In the same manner as Example 1, 390 grams (1.27 mole) of castor oil fatty acid was heated to form an estolide having an acid number of 45, which indicated that the estolide corresponded to the tetramer of castor oil fatty acid.

To the estolide obtained 42 grams (0.32 mole) of N,N-diethylaminopropylamine was added and the mixture was reacted in the same manner as Example 1. A yellow brown liquid having an amine number of 41 was obtained.

To 136 grams of the intermediate obtained was added 164 grams of monochloroacetic acid solution (9.5 grams of monochloroacetic acid and 8.5 grams of sodium bicarbonate in 146 grams of isopropyl alcohol). The reaction mixture was treated in the same manner as the previous examples and 142 grams of a brown liquid was obtained.

EXAMPLE 4

In the same manner as Example 1, 390 grams (1.26 mole) of hydrogenated castor oil fatty acid was heated to form an estolide having an acid number of 60, which indicated that the estolide corresponded to the trimer of hydrogenated castor oil fatty acid.

To the estolide obtained 43 grams (0.42 mole) of N,N-dimethylaminopropylamine was added and the mixture was reacted in the same manner as Example 1. A yellow brown liquid having an amine number of 56 was obtained.

To 100 grams of the intermediate obtained was added 148 grams of monochloroacetic acid solution (9.5 grams of monochloroacetic acid and 8.5 grams of sodium bicarbonate in 130 grams of isopropyl alcohol). The reaction mixture was treated in the same manner as the previous examples and 105 grams of a brown liquid was obtained.

EXAMPLE 5

In the same manner as Example 1, 670 grams (2.17 mole) of hydrogenated castor oil fatty acid was heated to form an estolide having an acid number of 35, which indicated that the estolide corresponded to the pentamer of hydrogenated castor oil fatty acid.

To the estolide obtained 43 grams (0.42 mole) of N,N-dimethylaminopropylamine was added and the mixture was reacted in the same manner as Example 1. A yellow brown liquid having an amine number of 38 was obtained.

To 206 grams of the intermediate obtained was added 173 grams of monochloroacetic acid solution (13 grams of monochloroacetic acid and 12 grams of sodium bicarbonate in 148 grams of isopropyl alcohol). The reaction mixture was treated in the same manner as the previous examples and 213 grams of a brown liquid was obtained.

EXAMPLE 6

In the same manner as Example 1, 204 grams (0.66 mole) of castor oil fatty acid and 95 grams (0.34 mole) of oleic acid were heated to form an estolide having an acid number of 90.

To the estolide obtained 50 grams (0.49 mole) of N,N-dimethylaminopropylamine was added and the mixture was reacted in the same manner as Example 1. A yellow brown liquid having an amine number of 96 was obtained.

To 175 grams of the intermediate obtained was added 183 grams of monochloroacetic acid solution (28 grams of monochloroacetic acid and 25 grams of sodium bicarbonate in 130 grams of isopropyl alcohol). The reaction mixture was treated in the same manner as the previous examples and 191 grams of a brown liquid was obtained.

EXAMPLE 7

In the same manner as Example 1, 242 grams (0.79 mole) of castor oil fatty acid was heated to get an estolide having an acid number of 60, which indicated that the estolide corresponded to the trimer of castor oil fatty acid.

To the estolide obtained 37 grams (0.26 mole) of N-aminopropylmorpholine was added and the mixture was reacted in the same manner as Example 1. A yellow brown liquid having an amine number of 52 was obtained.

To 162 grams of the intermediate obtained was added 157 grams of monochloroacetic acid solution (14 grams of monochloroacetic acid and 13 grams of sodium bicarbonate in 130 grams of isopropyl alcohol). The reaction mixture was treated in the same manner as the previous examples and 170 grams of a brown liquid was obtained.

COMPARATIVE EXAMPLE 1

305 grams (1.0 mole) of castor oil fatty acid and 107 grams (1.05 mole) of N,N-dimethylaminopropylamine were reacted in the same manner as Example 1. A yellow liquid having an amine number of 142 was obtained.

To 118 grams (0.3 mole) of the intermediate obtained was added 183 grams of monochloroacetic acid solution (28 grams of monochloroacetic acid and 25 grams of sodium bicarbonate in 130 grams of isopropyl alcohol). The reaction mixture was treated in the same manner as the previous examples and 135 grams of a brown liquid was obtained.

COMPARATIVE EXAMPLE 2

305 grams (1.0 mole) of castor oil fatty acid and 151 grams (1.05 mole) of N-aminopropylmorpholine were reacted in the same manner as Example 1. A yellow brown liquid having an amine number of 136 was obtained.

To 124 grams of the intermediate obtained was added 183 grams of monochloroacetic acid solution (28 grams of monochloroacetic acid and 25 grams of sodium bicarbonate in 130 grams of isopropyl alcohol). The reaction mixture was treated in the same manner as the previous examples and 141 grams of a brown liquid was obtained.

Tests and Results

Emulsion tests of the samples synthesized in comparison with lecithin and hydrogenated licithin were carried out as follows:

(1) Emulsion Test for Lanoline 8 parts of lanoline and 0.4 part of sample were placed in a beaker. Under enough agitation 16 parts of distilled water was added for 3 minutes. After additional 5 minute agitation, the mixture was poured into a test tube (16mm × 180 mm). Emulsion was observed after 10 minutes and 24 hours.

Estimation of emulsion =
100 × emulsion layer/total layer
Results of the test

| Sample | 10 minutes | 24 hours |
|---|---|---|
| Example 1 | 100% | 100% |
| Example 2 | 100% | 100% |
| Example 3 | 100% | 60% |
| Example 6 | 100% | 100% |
| Example 7 | 100% | 100% |
| Comparative Example 1 | 100% | 64% |
| Lecithin | 95% | 86% |

(2) Emulsion Test for Olive Oil

Test and estimation were carried out in the same manner as the test for lanoline.

Results of the test

| Sample | 10 minutes | 24 hours |
|---|---|---|
| Example 1 | 95% | 65% |
| Example 2 | 100% | 100% |
| Example 4 | 100% | 100% |
| Example 5 | 100% | 100% |
| Example 6 | 100% | 100% |
| Comparative Example 1 | 100% | 64% |
| Lecithin | 100% | 86% |
| Hydrogenated Lecithin | 100% | 60% |

(3) Emulsion Test for Isononyl Isononanoate

Test and estimation were carried out in the same manner as the test for lanoline.

Results of the test

| Sample | 10 minutes | 24 hours |
|---|---|---|
| Example 1 | 100% | 100% |
| Example 2 | 100% | 100% |
| Example 4 | 100% | 100% |
| Example 5 | 100% | 100% |
| Example 6 | 100% | 100% |
| Example 7 | 100% | 100% |
| Comparative Example 1 | 95% | 35% |
| Lecithin | 95% | 28% |
| Hydrogenated Lecithin | 85% | 25% |

(4) Suspension of Titanium Dioxide in Isopropyl Myristate 0.16 part of sample, 16 parts of isopropyl myristate and 1 part of titanium dioxide (MT-600SA made by Teika Company) were placed in a test tube (16mm × 180mm) and the mixture was agitated enough for 30 seconds. Suspension state was observed after 1 hour and 24 hours.

Estimation of suspension = 100 × (TLL − UCL)/TLL
TLL: total liquid layer
UCL: upper clear layer
Results of the test

| Sample | 1 hour | 24 hours |
|---|---|---|
| Example 1 | 100% | 100% |
| Example 2 | 100% | 100% |
| Example 4 | 100% | 100% |
| Example 5 | 100% | 100% |
| Example 6 | 100% | 100% |
| Example 7 | 100% | 100% |
| Comparative Example 1 | 33% | 27% |
| Comparative Example 2 | 38% | 28% |
| Lecithin | 91% | 25% |
| Blank | 32% | 27% |

(5) Compatibility with Esters

Compatibility with isononyl isononanoate and isopropyl myristate was tested at concentration of 33 % of sample in 67% of an ester and 66 % of sample with 34 % of an ester.

Results of the test

| Sample | | ININ | IPM |
|---|---|---|---|
| Example 1 | (33%) | miscible | miscible |
| | (66%) | miscible | miscible |
| Example 2 | (33%) | miscible | miscible |
| | (66%) | miscible | miscible |
| Example 4 | (33%) | miscible | miscible |
| | (66%) | miscible | miscible |
| Example 5 | (33%) | miscible | miscible |
| | (66%) | miscible | miscible |
| Example 6 | (33%) | miscible | miscible |
| | (66%) | miscible | miscible |
| Example 7 | (33%) | miscible | miscible |
| | (66%) | miscible | miscible |
| Comp. Ex. 1 | (33%) | immiscible | immiscible |
| | (66%) | immiscible | immiscible |
| Lecithin | (33%) | miscible | miscible |
| | (66%) | miscible | miscible |

(Note)
ININ: Isononyl isononanoate
IPM: Isopropyl myristate

From the data shown above, it is clear that the betaine compositions of the present invention provide lipophilic amphoteric surfactants having superior emulsifying property, supending property and compatibility with oily substances to ordinary amphoteric substances.

It is important that the lipophilic part of the present invention's amphoteric surfactant molecule includes acyl radicals of estolides, which make the present invention's amphoteric surfactants more lipophilic than ordinary amphoteric surfactants.

Chain length of $R_1$—CO can be varied, for example, from dimer having carbon number of 36 to hexamer having carbon number of 108 in the case of using castor oil fatty acid as a hydroxyfatty acid. This variation on lipophilic part of the molecule makes it possible that a wide range of lipophilic surfactants are provided by the technique of the present invention.

Additionally, reduced iodine value of these surfactants makes them stable against oxidation, and increased weight of these surfactants also promises reducing skin-irritation.

What is claimed is:

1. A lipophilic amphoteric surface active betaine compound of the formula

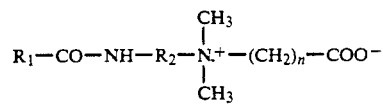

wherein $R_1$—CO is an acyl radical of an estolide, $R_2$ is an alkylene group having 1 to 3 carbon atoms and n is an integer from 1 to 3.

2. The betaine compound of claim 1, wherein the estolide is derived from a hydroxyfatty acid or a mixture of a hydroxyfatty acid and a fatty acid.

3. The betaine compound of claim 2, wherein the hyroxyfatty acid is castor oil fatty acid or hydrogenated castor oil fatty acid.

4. The betaine compound of claim 2, wherein the estolide has an acid number of 25 to 120.

5. A water-in-oil emulsion containing a non-polar substance, water and an emulsifying effective amount of the betaine compound of claim 5.

6. The emulsion of claim 5, wherein the non-polar substance is lanolin.

7. The emulsion of claim 5, wherein the non-polar substance is olive oil.

8. The emulsion of claim 5, wherein the non-polar substance is isononyl isononanoate.

9. The emulsion of claim 5, wherein the non-polar substance is isopropyl myristate.

* * * * *